United States Patent [19]
Moran, Jr.

[11] Patent Number: 5,310,905
[45] Date of Patent: May 10, 1994

[54] CONVERSION OF NYLON 6 AND/OR NYLON 6,6 TO MONOMERS

[75] Inventor: Edward F. Moran, Jr., Clarksboro, N.J.

[73] Assignee: E. I. Du Pont de Nemours and Company, Wilmington, Del.

[21] Appl. No.: 45,780

[22] Filed: Apr. 14, 1993

[51] Int. Cl.$^5$ .......................................... C07D 201/12
[52] U.S. Cl. .................................. 540/540; 540/538; 564/197; 562/590; 562/593
[58] Field of Search ................ 540/540, 538; 564/197; 362/590, 593

[56] References Cited

U.S. PATENT DOCUMENTS 3,069,465 12/1962 Monet ................................. 562/590

FOREIGN PATENT DOCUMENTS

| 910056 | 4/1954 | Fed. Rep. of Germany | 540/538 |
| 51-39684 | 4/1927 | Japan | 540/538 |
| 4550 | 1/1981 | Japan | 540/538 |

*Primary Examiner*—Robert T. Bond

[57] ABSTRACT

Waste nylon 6 and/or nylon 6,6 are treated with aliphatic monocarboxylic acid to depolymerize the polymer to desirable monomer.

5 Claims, No Drawings

CONVERSION OF NYLON 6 AND/OR NYLON 6,6 TO MONOMERS

BACKGROUND OF THE INVENTION

It has become increasingly important to salvage values from waste polymeric materials The production of monomers from waste polymer sources reduces the need to convert raw material from petroleum to the desired monomers at much greater time and expense. The provision of a new method to recover nylon values is a worthwhile objective. Since nylon 6 and nylon 6,6 share many market applications, e.g., carpets, the recovery of monomers from mixtures of nylon 6 and nylon 6,6 is particularly useful when recycling used consumer products because of the difficulty and expense of separating the nylons into their individual types.

SUMMARY OF THE INVENTION

The present invention provides a method for recovering caprolactam from waste polycaprolactam comprising supplying an acid of the formula

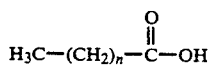

where n is 0 to 4 and the polycaprolactam to an autoclave in the amount of at least one mole of acid for every two moles of repeat units of the polymer, heating the mixture at a temperature of at least 150° C. and at autogenous pressure or greater for a time sufficient to depolymerize the polymer and form a mixture of caprolactam and a 6-alkylamidohexanoic acid and separating caprolactam from the mixture.

Also provided is a method for recovering adipic acid from waste polyhexamethylene adipamide comprising supplying an acid of the formula

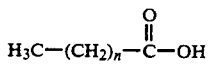

where n is 0 to 4 and the polyhexamethylene adipamide to an autoclave in the amount of at least two moles of acid for every mole of repeat units of the polymer, heating the mixture at a temperature of at least 150° C. and at autogenous pressure or greater for a time sufficient to depolymerize the polymer and form a mixture of adipic acid and N,N'-hexamethylene bisalkylamide and separating adipic acid from the mixture.

A further provision is a process for recovering caprolactam and adipic acid from waste containing both polycaprolactam and polyhexamethylene adipamide comprising supplying an acid of the formula

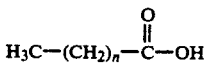

where n is from 0 to 4 and the mixture of the polymers to an autoclave in the amount of at least one mole of acid for every two moles of repeat units of polycaprolactam and at least two moles of acid for every mole of repeat units of polyhexamethylene adipamide and heating the mixture to a temperature of at least 150° C. and at autogenous pressure or greater for a time sufficient to depolymerize both polymers and form a mixture of caprolactam, 6-alkylamido-hexanoic acid, adipic acid and N,N'-hexamethylene bisalkylamide and separating caprolactam and adipic acid from the mixture.

DETAILED DESCRIPTION OF THE INVENTION

The present invention can be used to process either nylon 6 or nylon 6,6 alone or in any combination of the two. It accommodates the variability of feed which would be expected when mixed consumer and industrial nylon waste is processed. Surprisingly, it can convert a mixture of nylon 6 and nylon 6,6 to their respective monomers without prior separation of the polymers.

As applied to nylon 6, the process involves treating the nylon 6 (polycaprolactam) in an autoclave with an acid of the formula

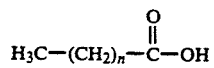

where n is an integer of from 0 to 4 and heating the mixture at a temperature of at least 150° C. Suitable aliphatic acids include acetic acid and propionic acid. The acid should be present in the amount of at least one mole of acid for every two moles of repeat units of the polymer. An excess of acid is employed to provide a solvent medium and to hasten the complete depolymerization of the nylon 6.

The rapidity of the process is affected by the temperature employed. While a temperature of 150° C. is useful, preferred are temperature in excess of 200° C. and preferably above 250° C. Ordinarily, the process proceeds at autogenous pressure, however while no benefit is known to result from it, greater pressure may be employed if desired. The mixture in the autoclave may be checked periodically and the process continued until depolymerization has taken place and caprolactam has been formed in substantial amounts. At this point, the autoclave is cooled and the caprolactam removed from its mixture with the other reaction product, 6-alkylamido-hexanoic acid, by steam distillation or by other means. The alkyl group corresponds to the alkyl chain of the carboxylic acid that was used to treat the polymer.

The process as applied to nylon 6,6 is quite similar to that with nylon 6 with two important exceptions. The first is that at least two moles of aliphatic carboxylic acid are required for every mole of repeat units of the nylon polymer. The second distinction is the end product which is a mixture of adipic acid and N,N'-hexamethylene bisalkylamide. The alkyl group corresponds to the alkyl chain of the carboxylic acid that was used to treat the nylon polymer.

It is where there is a mixture of both nylon 6 and nylon 6,6 waste polymer that the present invention is of particular advantage. Being able to process both in a single process without prior separation is of great benefit. The process proceeds in a similar manner to each of the recovery processes from nylon 6 and nylon 6,6 respectively as described above. The aliphatic acid should be added in an amount of at least one mole for every two moles of repeat units of the polycaprolactam present in the polymer mixture and at least two moles of the acid should be added for every mole of repeat units of the polyhexamethylene adipamide present in the polymer mixture. The resulting product contains both caprolactam and adipic acid in admixture with 6- alkylamidohexanoic acid and N,N'-hexamethylene bisalkylamide and they may be separated by procedures known to the art.

The invention is described further in the examples which follow. The examples are presented to illustrate but not to restrict the present invention. Parts and percentages are by weight unless otherwise noted.

EXAMPLES

Example 1

A 2 liter round bottom flask with a bottom drain heated with an electric heating mantle was set up. It included a thermocouple well in the flask to monitor temperature and a reflux condenser and was situated above a 600 ml steam jacketed filter funnel on a vacuum filter flask. A mechanical stirrer was also installed in the flask which was initially raised up high in the flask so that it could be lowered and used if necessary.

The flask was charged with 22.5 grams (0.2 mole) sheared nylon 6 carpet face fiber, 50.3 grams whole carpet containing 22.5 grams (0.1 mole) nylon 6,6 face fiber (cut into pieces to fit in the flask) and a mixture of 364.5 grams (6.1 mole) glacial acetic acid and 40.5 g water. The flask was heated electrically without stirring the contents. The filter funnel was heated by steam.

On heating, the nylon 6 started to dissolve at approximately 63° C. and on further increasing the temperature a positive indication of nylon 6,6 dissolution was observed at 86° C. On reaching 108° C., the paddle stirrer was lowered and rotated gently by hand to insure contact of all the residual backing with the solvent. Heating of the mixture was continued at 108° C. for 15 minutes and then the flask contents drained through the heated filter frit into the vacuum flask. On cooling to room temperature the filtrate solidified.

The filtrate obtained was easily melted at 80° C. and 215.6 grams of it was transferred to a pressure vessel and heated at 280° C. for 4 hours. The product from this treatment on cooling to room temperature was completely fluid. There was considerable spillage loss and the recovered product weighed 160.2 grams (74.3% of original charge). A gas chromatograph analysis of the product showed, in addition to the acetic acid solvent, the presence of only four compounds. They were identified as caprolactam, adipic acid, 6-acetamidohexanoic acid and N,N'-hexamethylenebisacetamide.

The acetic acid solvent was removed from the 160.2 grams of product solution by evaporation to give a concentrated product weighing 39.3 grams. Based on the estimated initial amount of nylon fiber charged, the total amount of filtrate obtained, the fraction used in this example, and the fraction recovered, the evaporated product should have weighed 34.1 grams. A quantitative Gas Chromatographic analysis of this product indicated that it contained 3.1% caprolactam, 17.2% adipic acid, 30.0% 6-acetamidohexanoic acid and 27.3% N,N'-hexamethylenebisacetamide.

Example 2

In a flask containing a mixture of 151.8 grams (2.0 mole) propionic acid and 16.9 grams of water there was placed 5 grams (0.04 mole) nylon 6 film and 5 grams (0.04 mole) nylon 6,6 staple fiber. This mixture was heated to 109° C. for 15 minutes at which point all of the nylon 6 film and the nylon 6,6 fibers had dissolved. On standing, the solution cooled to a waxy mush. A portion of this material was transferred to a pressure vessel and heated at 280° C. for 4 hours. The product from this treatment on cooling to room temperature was completely fluid. A gas chromatograph analysis of the product showed, in addition to the solvent, the presence of only four compounds. They were identified as caprolactam, adipic acid, 6-propionamide and N,N'-hexamethylene bispropionamide. After removal of the propionic acid solvent by evaporation the concentrated product analyzed 3.1% caprolactam, 10.3% adipic acid, 29.5% 6-propionamide-hexanoic acid and 22.2% N,N'-hexamethylene bispropionamide.

Example 3

A flask set-up similar to that of Example 1 was charged with 22.5 grams (0.2 mole) sheared nylon 6 carpet face fiber, 50.3 grams whole carpet containing 22.5 grams (0.1 mole) nylon 6,6 face fiber (cut into pieces to fit in the flask) and 810 grams of 88% formic acid (15.5 mole formic acid). The flask was heated electrically without stirring the contents. The filter funnel was heated by steam.

The nylon started to dissolve on initial contact. On reaching 87° C. the paddle stirrer was lowered and rotated gently by hand to insure contact of all the residual backing with the solvent. The mixture was heated to 105° C. over a 15 minute period and then the flask contents drained through the heated filter frit into the vacuum flask. On cooling to room temperature the filtrate remained fluid. The backing material remaining in the flask was essentially free of nylon face fiber.

A portion of the filtrate obtained was transferred to a pressure vessel and heated at 190° C. for 4 hours. The product from this treatment on cooling to room temperature was completely fluid. A gas chromatograph analysis of the product showed, in addition to the solvent, the presence of four compounds, only two of which were identified as caprolactam and adipic acid.

Examples 1–3 illustrate a process where the mixture of nylon 6 and nylon 6,6 are first separated from consumer waste, e.g., used carpet or carpet scrap, by extraction with aliphatic monocarboxylic acid. The filtrate comprising the acid and the extracted nylon 6 and nylon 6,6 are used directly in the depolymerization process of this invention.

I claim:

1. A process for recovering caprolactam from waste polycaprolactam comprising supplying an acid of the formula

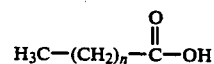

where n is 0 to 4 and the polycaprolactam to an autoclave in the amount of at least one mole of acid for every two moles of repeat units of the polymer, heating the mixture at a temperature of at least 150° C. and at autogenous pressure or greater for a time sufficient to depolymerize the polymer and form a mixture of caprolactam and a 6-alkylamidohexanoic acid and separating caprolactam from the mixture.

2. A process according to claim 1 wherein the waste polycaprolactam is the pile fiber of carpets.

3. A process for recovering adipic acid from waste polyhexamethylene adipamide comprising supplying an acid of the formula

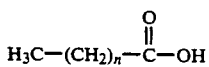

where n is 0 to 4 and the polyhexamethylene adipamide to an autoclave in the amount of at least two moles of acid for every mole of repeat units of the polymer, heating the mixture at a temperature of at least 150° C. and at autogenous pressure or greater for a time sufficient to depolymerize the polymer and form a mixture of adipic acid and N,N'-hexamethylene bisalkylamide and separating adipic acid from the mixture.

4. A process according to claim 3 wherein the waste polyhexamethylene adipamide is the pile fiber of carpets.

5. A process for recovering caprolactam and adipic acid from waste containing both polycaprolactam and polyhexamethylene adipamide comprising supplying an acid of the formula

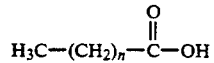

where n is 0 to 4 and the mixture of the polymers to an autoclave in the amount of at least one mole of acid for every two moles of repeat units of polycaprolactam and at least two moles of acid for every mole of repeat units of polyhexamethylene adipamide and heating the mixture to a temperature of at least 150° C. and at autogenous pressure or greater for a time sufficient to depolymerize both polymers and form a mixture of caprolactam, 6-alkylamidohexanoic acid, adipic acid and N,N'-hexamethylene bisalkylamide and separating caprolactam and adipic acid from the mixture.

* * * * *